United States Patent [19]

Ohnishi

[11] Patent Number: 5,060,281
[45] Date of Patent: Oct. 22, 1991

[54] METHOD AND APPARATUS FOR DETECTING DISPARITY OF CYCLIC LENGTH OF PRINTED PATTERNS

[75] Inventor: Ryuji Ohnishi, Takamatsu, Japan

[73] Assignee: Futec, Inc., Kagawa, Japan

[21] Appl. No.: 658,450

[22] Filed: Feb. 22, 1991

Related U.S. Application Data

[63] Continuation of Ser. No. 207,969, Jun. 17, 1988, abandoned.

[30] Foreign Application Priority Data

Oct. 15, 1987 [JP] Japan .................. 62-260157

[51] Int. Cl.$^5$ .............................................. G06K 9/00
[52] U.S. Cl. ...................................... 382/34; 382/22; 382/57; 358/106
[58] Field of Search ............... 382/10, 34, 22, 57, 382/8; 358/106; 356/237

[56] References Cited

U.S. PATENT DOCUMENTS

| | | | |
|---|---|---|---|
| 4,136,332 | 1/1979 | Kadota et al. | 382/34 |
| 4,349,880 | 9/1982 | Southgate et al. | 364/507 |
| 4,561,103 | 12/1985 | Horiguchi et al. | 382/34 |
| 4,626,907 | 12/1986 | Schedewie | 358/106 |
| 4,701,859 | 10/1987 | Matsuyama et al. | 382/34 |
| 4,724,481 | 2/1988 | Nishioka | 358/106 |
| 4,805,224 | 2/1989 | Koezuka et al. | 382/34 |
| 4,835,720 | 5/1989 | Ditto et al. | 382/34 |

FOREIGN PATENT DOCUMENTS 0225651 6/1987 European Pat. Off. .
53-110547 9/1978 Japan .

OTHER PUBLICATIONS

Thomas, "Defect Scanner for Repetitive Patterns", Mar., 1974, vol. 16, No. 10, p. 3158, IBM Technical Disclosure Bulletin.

Primary Examiner—Michael Razavi
Assistant Examiner—Yon Jung
Attorney, Agent, or Firm—Joseph Scafetta, Jr.

[57] ABSTRACT

A method of detecting a disparity in a cyclic length of a printed pattern includes the steps of scanning a to-be-checked sheet on which predetermined patterns are cyclically printed in the longitudinal direction by an electronic camera to obtain image data corresponding to a pattern, extracting outline data representing an outline of the pattern from the image data, writing the outline data extracted in the extraction step into a memory with a predetermined cycle in accordance with travel position data of the to-be-checked sheet, reading out the outline data, and comparing first outline data for one cycle read out from the memory and second outline data which is read out after the first outline data is read out. Disparity of a cyclic length of the pattern is detected based on a correlation between the first and second outline data, e.g., a coincidence or noncoincidence therebetween, in accordance with the comparison result in the comparison step.

8 Claims, 3 Drawing Sheets

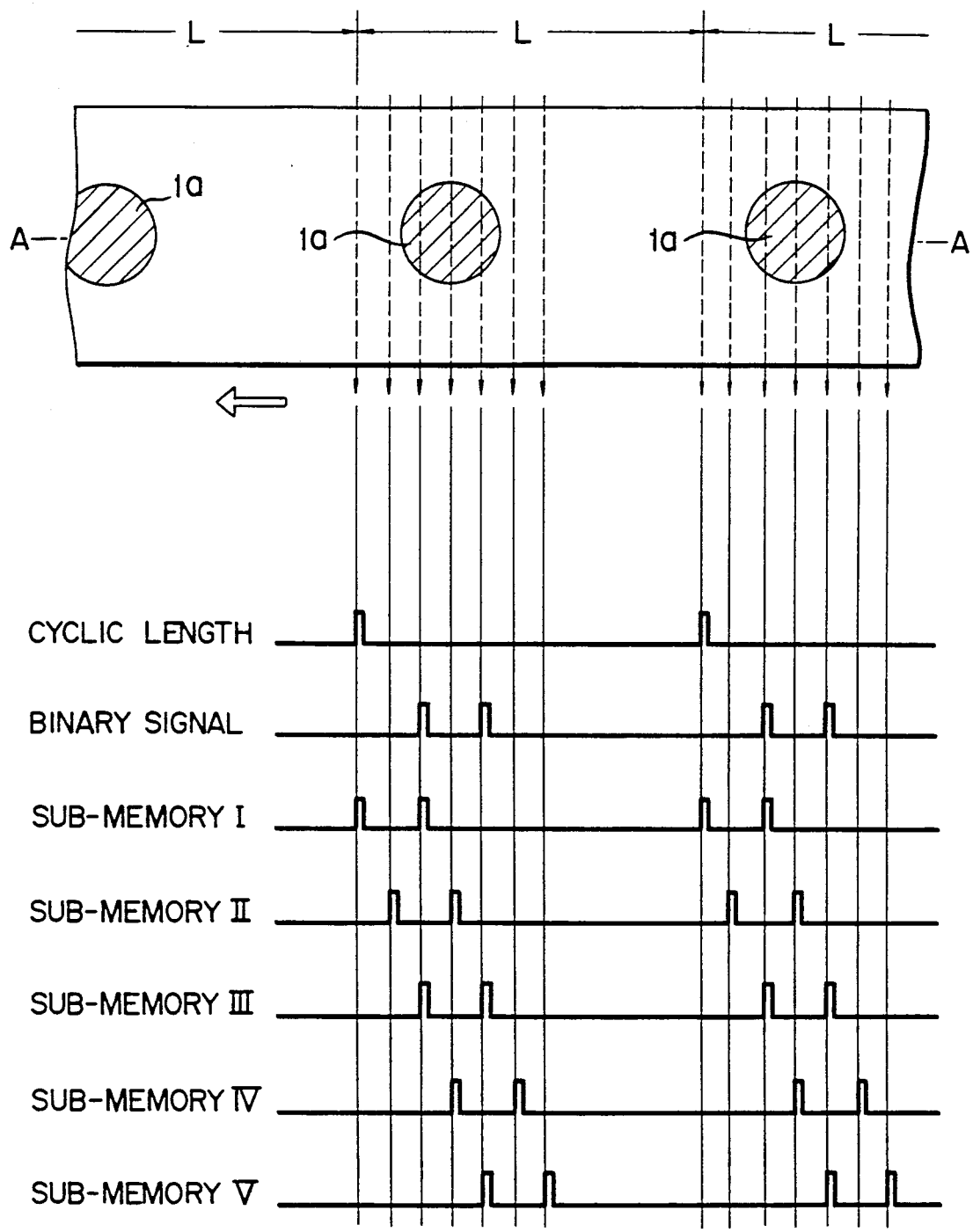
F I G. 2

METHOD AND APPARATUS FOR DETECTING DISPARITY OF CYCLIC LENGTH OF PRINTED PATTERNS

This is a continuation of application Ser. No. 07/207,969, filed June 17, 1988, which was abandoned upon the filling hereof.

CROSS-REFERENCE TO RELATED APPLICATION

This application is related to U.S. patent application Ser. No. 07/208,097 filed concurrently herewith on June 17, 1988, now U.S. Pat. No. 4,975,971, in the name of the same inventor for an invention entitled "Method and Apparatus for Detecting Significant Difference in Sheet Material".

Background of the Invention

1. Field of the Invention

The present invention relates to a method and apparatus for detecting a disparity in cyclic lengths of printed patterns of a printed sheet on which predetermined patterns are cyclically printed in the longitudinal direction of the printed sheet during travel of the printed sheet.

2. Description of the Related Art

Japanese Patent Application No. 62-258683 (filed on Oct. 14, 1987) discloses a method for detecting a defect on a printed sheet. In this method, when a defect on a printed sheet is detected during sheet travel, an outline of a printed pattern is extracted by signal processing, and a mask zone corresponding to the outline of the printed pattern is set. After the mask zone is enlarged, pattern data for one cycle including the enlarged mask zone is stored in a memory. Thereafter, pattern data for the next cycle is compared with the previous pattern data stored in the memory. Thus, a printed portion of the pattern for the next cycle is masked by the mask zone, and a defect on the printed sheet is detected by comparing signal components excluding the mask zone.

In the printed sheet defect detection method in the associated application, printed patterns must have a predetermined cyclic length. When this condition is not satisfied, a mask zone set for the next cyclic pattern does not coincide with a printed pattern included in the next cyclic pattern, and at least a portion of the printed pattern falls outside this zone along the feed direction. This may lead to a detection error.

Because a printed sheet travels, the printed sheet is expanded or shrunk due to variations in conditions such as tension acting on the sheet, temperature, humidity, and the like, or due to the influence of the material, thickness and the like of the sheet. Thus, an actual cyclic length of the printed pattern during travel is often different from a value measured in advance in a non-travel state of the printed sheet. In this manner, when the cyclic length of the printed pattern varies, a portion falling outside the mask zone is erroneously detected as a defect.

If a disparate amount of the cyclic length of the printed pattern of a traveling sheet can be detected, the preset cyclic length of a defect detection apparatus can be adjusted during inspection in accordance with the detected amount of disparity, and a detection error can be prevented. Thus, desired defect detection can be realized.

However, since a method for detecting a disparate amount of a cyclic length of a printed pattern of a traveling sheet is not known yet, it is impossible to check the preset cyclic length of the defect detection apparatus during inspection. For this reason, a variation in cyclic length of the printed pattern degrades defect detection precision of a printed sheet.

SUMMARY OF THE INVENTION

It is an object of the present invention to provide a method and can apparatus for detecting a disparity in a cyclic length of a printed pattern, which can detect a disparity amount of a cyclic length of a printed pattern during travel of a printed sheet.

According to the present invention, the surface of a printed sheet on which predetermined patterns are cyclically printed in the longitudinal direction is imaged by an electronic camera during the travel of the sheet. An image signal output from this camera and corresponding to a cyclic length of the printed pattern is sequentially stored in a memory in synchronism with the travel of the printed sheet. In this case, the content of the memory is sequentially updated by the input image signal. The cyclic length of the stored image signal serves as a reference cyclic length, and the cyclic length of the next image signal obtained by the camera is compared with that of the previous image signal, i.e., the reference cyclic length. More specifically, the reference-cyclic-length signal is stored in a multistage memory, and the cyclic-length-signals corresponding to input image signals are shifted by a predetermined pitch along the travel direction and stored in the multistage memory. The reference cyclic length is thus compared with the next cyclic length. Alternatively, the next cyclic length is shifted y a shift register in synchronism with the travel of the printed sheet, and the output from the shift register is compared with the reference cyclic length. Upon this comparison, a coincidence/noncoincidence between the reference and the next cyclic lengths is detected, and a disparate amount of the next cyclic length with respect to the reference cyclic length is detected.

The electronic camera images the surface of the printed sheet, on which printed patterns are cyclically printed in the longitudinal direction, during the travel of the sheet. An image signal output from the camera is sequentially stored in the memory in synchronism with the travel of the printed sheet. In this case, the memory content is sequentially updated by the input image signal. The write access to the memory is executed for one cyclic length of the printed pattern. The camera continuously images the printed sheet, and outputs an image signal for the next cyclic length to a path including the memory and a path including no memory.

The next cyclic length of the image signal output onto the memory path is stored as a reference cyclic length. At the same time, the previously stored content is read out. The next cyclic length of an image signal output onto the nonmemory path is compared with the reference cyclic length read out from the memory. That is, the next cyclic length of the latest image data is compared with the previous cyclic length, this detecting a disparate amount of the next cyclic length with respect to the reference cyclic length.

BRIEF DESCRIPTION OF THE DRAWINGS

FIG. 2 is a view showing a plurality of scanning lines scanning a portion of a printed sheet and image signals corresponding to the scanning lines.

DETAILED DESCRIPTION OF THE PREFERRED EMBODIMENTS

Figure 1:
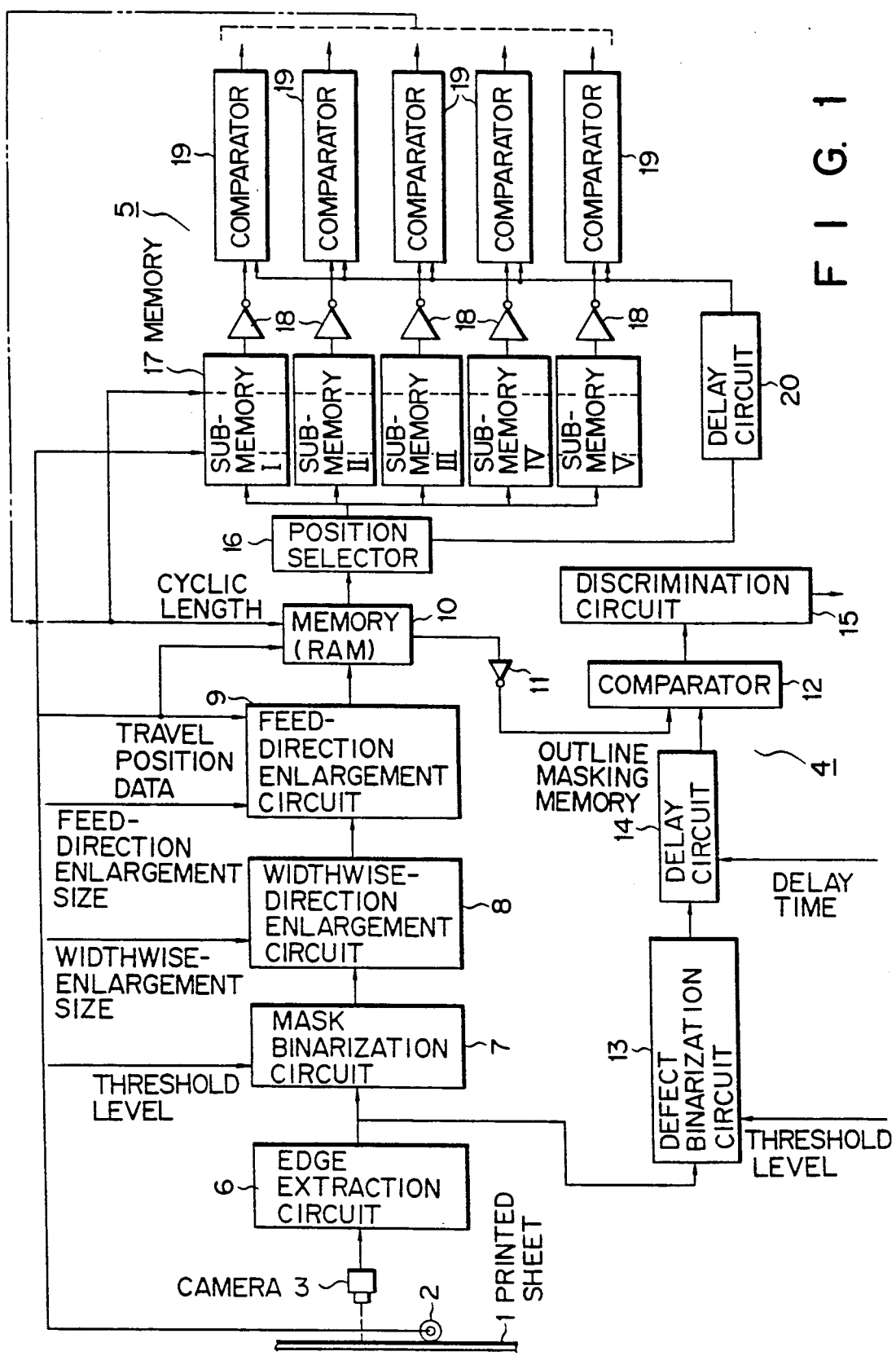
FIG. 1 is a block diagram showing, a circuit of an apparatus for practicing a method for detecting a disparate amount of printed patterns according to an embodiment of the present invention, and an apparatus for detecting a defect of a to-be-checked material.

As shown in FIG. 2, prints 1a such as letters, patterns, and the like are cyclically printed on printed sheet 1 shown in FIG. 1 at cyclic lengths L. Printed sheet 1 travels in its longitudinal direction, and travel data is detected by a pulse generator 2 (FIG. 1) comprising, e.g., a rotary encoder.

The surface of the printed sheet 1 is imaged by an electronic camera 3 for receiving light reflected by or transmitted through the surface. Camera 3 incorporates a linear image sensor array, and scans the surface of the traveling printed sheet 1 along the widthwise direction. In FIG. 2, dotted arrows indicate scanning positions, and a solid arrow indicates a travel direction of the sheet 1.

The image signal from the camera 3 is processed by a detection apparatus comprising a defect detection apparatus 4 and an apparatus 5 for detecting a disparate amount of a cyclic length of the printed patterns shown in FIG. 1. Defects on the sheet 1 are detected by the apparatus 4, and a disparate amount of the cyclic length L is detected by the apparatus 5.

Defect detection apparatus 4 will be described below.

Defect detection apparatus 4 comprises an outline extraction circuit 6, a mask binarization circuit 7, a widthwise-direction enlargement circuit 8, a feed-direction enlargement circuit 9, a memory 10, an inverter 11, a comparator 12, a defect binarization circuit 13, a delay circuit 14, and a discrimination circuit 15.

Outline extraction circuit 6 comprises, e.g., a differential circuit, and is connected to the output terminal of the camera 3. Extraction circuit 6 retrieves all the image signals from the camera 3, and emphasizes a change in signal, thus extracting outlines of the print 1a and a defect.

Mask binarization circuit 7 is connected to the output terminal of the outline extraction circuit 6 and converts a signal exceeding a threshold level into a binary signal. The threshold level is selected in accordance with the density of the print 1a during initialization of the detection apparatus 4.

Widthwise-direction enlargement circuit 8 is connected to the output terminal of a binarization circuit 7, and enlarges the output signal from circuit 7 by an estimated deviation in the widthwise direction in accordance with the state of a conveying path along which the sheet 1 travels in order to prevent a detection error due to zig-zag travel of the sheet 1 within the cyclic length L. The enlargement size corresponds to several bits to the right and left in the widthwise direction, and is selected during initialization of apparatus 4.

Feed-direction enlargement circuit 9 is connected to the output terminal of the circuit 8, and enlarges the output signal from the circuit 7 by an estimated deviation in the feed (travel) direction in accordance with the state of the conveying path along which the sheet 1 travels, in order to prevent a detection error due to a deviation in the feed (travel) direction within one cyclic length L of the sheet 1 The enlargement size is determined in accordance with the number of pulses from the pulse generator 2, and is selected during initialization of the apparatus 4. Circuit 9 also receives travel position data determined by the output pulses from the pulse generator 2.

Memory 10 comprises, e.g., a RAM which can simultaneously perform write and read access operations by scrolling. The output from the outline extraction circuit 6 is sequentially written in the memory 10 through the circuits 7, 8, and 9. Memory 10 receives travel position data determined by the output pulses from the pulse generator 2, and performs write access in synchronism with this travel position data.

Cyclic length L obtained by actually measuring a length of one cycle of the print 1a on the printed sheet 1 is stored in the memory 10 when the apparatus 4 is initialized. Memory 10 has a capacity capable of storing pattern data for one cycle of the sheet 1.

Signals sequentially read out from the memory 10 are mask data for an outline mask. The output from the memory 10 is supplied to and is inverted by the inverter 11. The output terminal of the inverter 11 is connected to the comparator 12. Comparator 12 comprises an AND gate, and compares the outline mask output read out from the memory 10 and the output from the defect binarization circuit 13 to detect a defect.

Defect binarization circuit 13 is connected to the output terminal of the outline extraction circuit 6, and converts a signal exceeding a threshold level into a binary signal. The threshold level is higher than that of the circuit 7, and is selected to be a predetermined value in accordance with the density of the print 1a when the apparatus 4 is initialized. Circuit 13 binarizes pattern tern data for the next cycle scanned (monitored) by the camera 3 to be delayed from the cycle written in the memory 10 by, e.g., one cycle.

Delay circuit 14 connected to the output terminal of the circuit 13 delays the output from the circuit 13 by a time corresponding to a processing time in the circuits 8 and the 9 and memory 10, and outputs the delayed output to the comparator 12.

Discrimination circuit 15 is connected to the output terminal of the comparator 12, and determines width or length of a detected defect based on the comparison result from the comparator 12. In this case, the width of the defect is obtained by measuring a pulse width of the significant signal, while the length of the defect is measured by counting scanning lines which scan the defect.

Detection apparatus 4 with the above arrangement detects a defect on the surface of a to-be-checked material as follows. That is, during defect detection, necessary initialization is performed, that is, predetermined cyclic length L of the print 1a printed on the printed sheet 1 is actually measured, and is set in the memory 10 by key inputs. The threshold levels are respectively set in the binarization circuits 7 and 13 by key inputs, and enlargement sizes in the widthwise and feed directions are respectively set in the enlargement circuits 8 and 9 by key inputs.

Upon initiation of detection after the initialization, the surface of the traveling printed sheet 1 is scanned in the widthwise direction by the electronic camera 3. Upon scanning, the camera 3 outputs an image signal. All the image signals are retrieved and differentiated by the outline extraction circuit 6. With this processing, a change in image signal is emphasized, thus detecting an outline of the print 1a printed on the printed sheet 1.

In order to mask the printed pattern 1a on the surface of the printed sheet 1 along its outline, an extracted outline mask differentiated signal is inputted to the mask binarization circuit 7, and is converted to a mask binary signal. The mask binary signal is inputted to the widthwise-direction enlargement circuit 8, and is enlarged by several bits in the widthwise direction. The mask binary signal is inputted to the feed-direction enlargement circuit 9, and is enlarged in the feed direction by one output pulse (one scanning) of the pulse generator 2. This enlargement processing is performed as follows. That is, the mask binary signal is shifted in the feed direction, and the shifted signal is added to the original binary signal.

With the above-mentioned enlargement processing, a mask zone is enlarged in the widthwise and feed directions for an outline mask of the print 1a. As a result, a deviation of the printed sheet 1 within one cyclic length L caused by slight zig-zag travel, expansion, a change in travel speed, and the like of the printed sheet 1 can be ignored, and outline masking stability can be improved.

Pattern data for one cycle including outline mask data of the print 1a obtained as described above is sequentially written in the memory 10 in accordance with the travel position data of the sheet 1 detected by the pulse generator 2. Thus, an outline mask signal for the printed pattern 1a is formed in the memory 10. More specifically, first one cyclic length L of the printed sheet 1 is scanned by the camera 3, and pattern data of the printed pattern 1a to be masked is stored in the memory 10 on the basis of the image signal obtained by the camera 3. The storage content serves as a reference pattern for defect detection (to be described later).

The reference pattern is automatically set as described above, and the next one cyclic length of the printed sheet 1 is subsequently scanned by the camera 3. If this cycle includes a defect, the camera 3 outputs an image signal including a defect signal component. The image signal is retrieved and differentiated by the outline extraction circuit 6. Thus, an outline of a defect can be extracted together with the outline of the pattern 1a printed on the printed sheet 1.

Pattern data for one cycle including the printed pattern 1a to be masked and defect data is enlarged in the widthwise and feed directions, and is sequentially written in the memory 10 to be automatically updated in accordance with the travel position data of the printed sheet 1 by scrolling. Simultaneously, the memory 10 outputs the previously stored pattern data for the preceding cycle to the comparator 12 as an outline mask signal through the inverter 11.

The output having defect data from the outline extraction circuit 6 is also inputted to the defect binarization circuit 13. The output from the outline extraction circuit 6 is an output scanned by the camera 3. The output is converted to a binary signal by the binarization circuit 13, and is then inputted to the comparator 12 through the delay circuit 14 to be synchronized with the readout timing of the outline mask signal.

Comparator 12 compares the pattern data of the preceding cycle as reference data with pattern data for the next cycle which is being scanned by the camera 3. Only when the inverted background base signal of the reference pattern coincides with the defect signal, comparator 12 generates a defect detection signal indicating defect detection. The defect detection signal is inputted to the discrimination circuit 15, and the length or width of the defect is determined and is outputted to a recording unit such as a printer.

According to the defect detection method described above, since outlines of the prints 1a are automatically retrieved and stored in the memory 10, positions of the printed patterns 1a need not be individually designated, and position data need not be prestored. That is, cyclic length L need only be set in the memory 10. Therefore, when defect detection of a large number of types of printed sheets or a printed sheet on which complicated printed patterns 1a are printed is to be performed, defect detection can be automatically performed by only setting cyclic length L in the memory 10. Therefore, the operation of the detection apparatus can be facilitated. Since the mask zone of the printed pattern 1a is used as an outline mask, a masking area can be reduced, and hence, an area to be detected can be increased, thus improving detection reliability. Since defect detection is performed by a reference pattern which is read out from the memory 10 in response to write access of the memory 10 and the latest pattern corresponding to a latest image signal output from the camera 3, defect detection can be performed in real time. Thus, high-speed defect detection can be achieved.

Disparity amount detection apparatus 5 practices the method of the present invention. Apparatus 5 comprises a position selector 16, multistage submemories I to V of a memory 17, inverters 18, comparators 19, and a delay circuit 20.

Position selector 16 selects an arbitrary position in the widthwise direction of the printed sheet 1 from pattern data for one cycle stored in the memory 10, and extracts continuous data at the selected position along the travel direction of the sheet 1. Selector 16 extracts bit data in the memory 10 corresponding to, e.g.. line A—A in FIG. 2.

Position selection of cyclic length detection data is performed as follows. That is, a position having the highest wiring frequency of the printed pattern 1a is selected in advance during initialization of the apparatus 5 in accordance with the position of the printed pattern 1a. Position selector 16 comprises an OR gate for eliminating the influence of the zig-zag travel of the printed sheet 1. Selector 16 selects several adjacent bits in the widthwise direction as a selection position, and outputs these cyclic length detection data through the OR gate.

Submemories I to V of the memory 17 receive the outputs from the position selector 16. An odd number of submemories I to V are prepared. Cyclic lengths based on the actually measured values of the sheet 1 are respectively set in the submemories I to V. Submemories I to V are constituted by memories which are shifted in advance by, e.g., one scan interval in the travel direction of the printed sheet 1 in correspondence with the output pulses from the pulse generator 2. If a scan interval is 1 mm, the address of submemory II is shifted from center submemory III in a "+" direction by one scan interval (i.e., 1 mm with respect to reference phase-shift memory III), and the address of submemory I is shifted by two scan intervals in the "+" direction (i.e., 2 mm with respect to reference submemory III). The address of submemory IV is shifted in a "−" direction by one scan interval (i.e., 1 mm with respect to reference phase shift memory III), and the address of submemory V is shifted in the "−" direction by two scan intervals (i.e., 2 mm with respect to reference submemory III). Submemories I to V receive travel position data obtained by the output pulses from the pulse generator 2. Cyclic length detection data from the position selector 16 are respectively written in the submemories in synchronism with the travel position data.

Inverters 18 are respectively connected to the output terminals of submemories I to V, and invert the outputs from submemories I to V. The output terminals of the inverters 18 are connected to one of two input terminals of the comparators 19. Each comparator 19 comprises an AND gate, and compares the cyclic length detection data read out from one of the submemories I to V with cyclic length detection data (reference cyclic length) read out from the memory 10 by the position selector 16 and inputted to the other input terminal of the comparator 19 through the delay circuit 20. The cyclic length detection data input through the delay circuit 20 is the latest outline pattern data output from the camera 3. The reference cyclic length data read out from the submemories I to V correspond to pattern data for a previous cycle of the latest data, e.g , for the immediately preceding cycle.

Delay circuit 20 connected to the output terminal of the position selector 16 delays the latest pattern data from the selector 16 by a time corresponding to a processing time of the submemories I to V and the inverters 18. The delayed pattern data is inputted to the comparators 19.

In the apparatus 5 for detecting a disparate amount of a cyclic length described above, cyclic length detection data for one cycle of the printed pattern la passing through line A—A in FIG. 2 of the printed sheet 1 are read out by the position selector 16 from the pattern data for one cycle stored in the memory 10 of the defect detection apparatus, and the readout data are stored in the submemories I to V of the memory 17, respectively. FIG. 2 illustrates the storage states in the submemories I to V. These storage contents serve as reference cyclic length data.

The next cyclic length data of the printed pattern la extracted from the memory 10 by the selector 16 from the next pattern data continuously outputted from the camera 3 are output to the comparators 19 through the memory 17, and are also outputted thereto through the delay circuit 20. The next cyclic length data through the memory 17 are respectively stored in the submemories I to V of the memory 17 as the next reference cyclic length data. At the same time, the previously stored contents are read out from the submemories I to V and are inputted to the comparators 19 through the inverters 18. The next cyclic length data supplied to the delay circuit 20 are delayed by a predetermined period of time by the delay circuit 20 to be synchronized with a readout timing of the cyclic length detection data (reference cyclic length). The delayed data are then inputted to the comparators 19, and are compared with the reference cyclic length data read out from the memory 17.

Upon this comparison, a difference between the next cyclic length data of the latest pattern output from the camera 3 and the previous cyclic length data is detected, thereby detecting a disparate amount of the next cyclic length with respect to the reference cyclic length. More specifically, if the binary signal representing the next cyclic length and passing through the selector 16 has a waveform shown in FIG. 2, the comparator 19 connected to the submemory III whose timing coincides with the binary signal satisfies its AND condition, and it is detected based on the output from the comparator 19 that the next cyclic length is not deviated from the reference cyclic length. Therefore, if the AND condition is satisfied in any of the comparators 19 connected to other submemory positions II, IV, and V, the presence/absence of disparity, a disparity direction, and a disparate amount of the cyclic length can be detected based on the output from the corresponding comparator 12.

Figure 3:
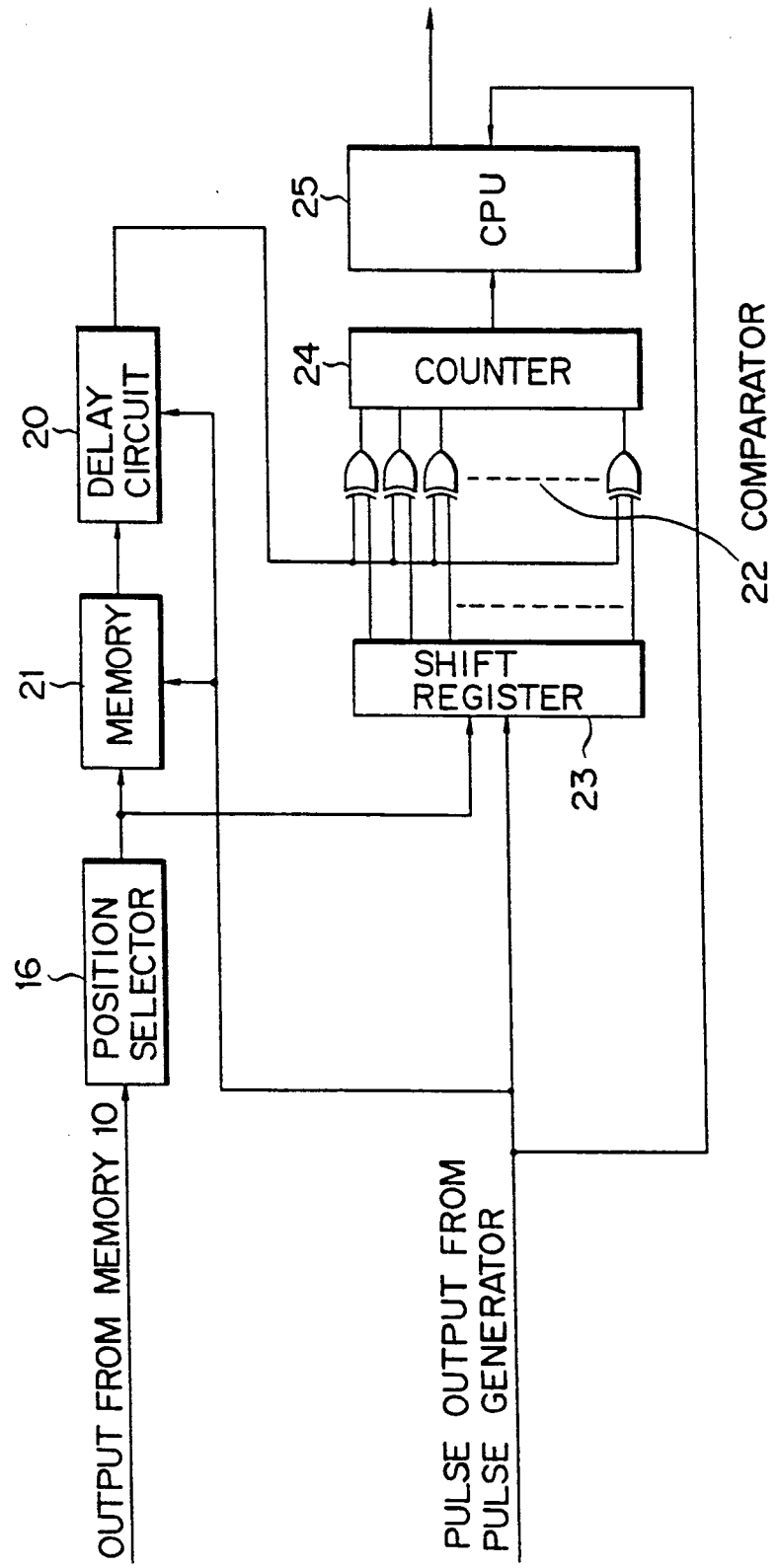
FIG. 3 is a block diagram of an apparatus for practicing a method for detecting a disparate amount of patterns according to another embodiment of the present invention.

The present invention can be carried our as shown in FIG. 3.

The output terminal of the position selector 16 for extracting the reference cyclic length from the pattern data stored in the memory 10 is connected to the memory 21 comprising a RAM. The output terminal of the memory 21 is connected to the comparators 22 through the delay circuit 20. Comparators 22 comprise EX-OR gates corresponding in number to the number of shift stages of a shift register 23 to be described below. Register 23 shifts a cyclic length (cyclic length) On the latest sheet surface imaged by the camera 3 in response to pulses from the pulse generator 2. The number of shift stages is an odd number, e.g., 15. With the shift operation, the latest extracted data is developed along the longitudinal direction of the printed sheet 1. The register outputs from the shift register 23 are respectively inputted to the comparators 22. The output terminals of the comparators 22 are connected to a counter 24. When the outputs from the comparator 22 indicate a noncoincidence, the counter 24 counts the comparison outputs from the comparators 22 for every shift. Counter 24 is connected to a CPU 25. CPU 25 discriminates a cyclic length based on the output from the counter 24.

In this embodiment, cyclic length data of the latest printed sheet portion imaged by the camera 3 is shifted by the shift register 23 in synchronism with the travel of the printed sheet 1, and is sequentially inputted to the comparators 22. At the same time, previous cyclic length data (reference cyclic length data) associated with the previous pattern data stored in the memory 21 is delayed by the delay circuit 20 in synchronism with the travel of the printed sheet 1 and are inputted to the comparators 22. The results from these comparators 22 re counted by the counter 24. The count value indicates a small value when the reference cyclic length coincides with the next cyclic length compared with the reference cyclic length; otherwise, the count indicates a large value. The count value is supplied to the CPU 25. When the CPU 25 receives the small count value, it determines that the input cyclic length is most approximate to the reference cyclic length, and outputs the determination result to an external circuit.

In this embodiment, the object of the present invention can be achieved as described above. The latest next cyclic length which is being scanned by the camera 3 is developed in the shift register 23, and the developed cyclic length data is compared with the reference cyclic length data. Thus, the format of the memory 21 can be simplified.

A disparate amount of a printed pattern cyclic length detected by the arrangement of each embodiment described above is outputted to a circuit outside the disparity amount detection apparatus, and is displayed on a display using, e.g., an LED. Thus, when a user judges that a disparate amount falls outside an enlarged mask zone, he corrects a preset cyclic length in the memory 10 in accordance with the detected disparate amount. Alternatively, a preset cyclic length in the memory 10 is automatically corrected through an appropriate correction circuit (not shown) in accordance with the disparate amount outputted from the disparate amount detection apparatus 5.

In each of the above embodiments, a binary signal obtained by processing in the defect detection apparatus 5 is utilized. However, in the disparate amount detection of this invention, a signal different from that in defect detection may be used. A signal retrieved by the position selector may be an analog signal.

According to the present invention as described above, the surface of a printed sheet on which printed patterns are cyclically printed in the longitudinal direction is scanned by an electronic camera during travel of the sheet. An image signal output from the camera and corresponding to the cyclic length of a printed pattern is sequentially stored in a memory in synchronism with the travel of the printed sheet. In this case, the storage content of the memory is sequentially updated by the input image signal. The cyclic length stored in the memory, i.e., the reference cyclic length is compared with the next cyclic length, and a disparate amount of a printed pattern cyclic length can be detected based on a difference between the cyclic lengths during the travel of the printed sheet.

What is claimed is:

1. A method of detecting a disparity in a cyclic length of a pattern, comprising the steps of:
    moving a to-be-checked sheet on which predetermined patterns are cyclically printed in a longitudinal direction of travel;
    scanning said to-be-checked sheet by means for obtaining image data corresponding to the pattern;
    extracting from the image data output data representing an outline of the pattern;
    obtaining movement position data indicating different movement positions of said to-be-checked sheet;
    writing the outline data, extracted in the extracting step, into storage means as reference outline data;
    updating, for every cycle, the reference outline data stored in the storage means such that the reference outline data becomes outline data corresponding to a cycle which precedes a current cycle by at least one cycle in accordance with the movement position data;
    reading out the reference outline data from said storage means into a comparator;
    comparing current outline data corresponding to a current cycle with updated reference outline data read out from the storage means, in order to obtain a comparison result; and
    detecting a disparity in the cyclic length of the pattern from a correlation between the current outline data and the updated reference outline data, in accordance with the comparison result obtained by said comparator.

2. A method according to claim 1, wherein said comparing step includes the substeps of:
    reading the current outline data as a plurality of suboutline data corresponding to the different movement positions,
    storing the suboutline data into substorage means, and
    comparing the suboutline data with the updated reference outline data,
    wherein the disparity detecting step comprises the substep of:
    determining a disparate amount of the cyclic length, in accordance with the suboutline data which coincide with the updated reference outline data.

3. A method according to claim 2, wherein the storing substep comprises the substep of:
    storing the suboutline data into a plurality of submemories,
    wherein the comparing step further comprises the substep of:
    comparing the suboutline data in said submemories with the updated reference outline data.

4. A method according to claim 1, wherein the comparing step comprises the substeps of:
    shifting a plurality of components of the current outline data and the updated reference outline data in accordance with the movement position data to obtain sequentially outline data components, and
    comparing sequentially the outline data components of the updated reference outline data with the outline data components of the current outline data, and
    wherein the disparity detecting step comprises the substep of:
    determining a disparate amount based on a number of coincidences between the outline data components of the current outline data and the updated reference outline data.

5. An apparatus for detecting a disparity in a cyclic length of a pattern, said apparatus comprising:
    means for moving a to-be-checked sheet on which predetermined patterns are cyclically printed in a longitudinal direction of travel;
    means for scanning said to-be-checked sheet to output image data corresponding to the pattern;
    means for extracting from the image data outline data representing an outline of the pattern;
    means for outputting movement position data indicating different movement positions of said to-be-checked sheet;
    means for storing the outline data extracted by the extracting means as reference outline data;
    means for updating, for every cycle, the reference outline data stored in the storage means such that the reference outline data becomes outline data corresponding to a cycle which precedes a current cycle by at least one cycle;
    means for comparing current outline data corresponding to a current cycle with the updated reference outline data read out from the storing means, in order to obtain a comparison result; and
    means for detecting a disparity in a cyclic length of the pattern from a correlation between the current outline data and the updated reference outline data, in accordance with the comparison result obtained by said comparing means.

6. An apparatus according to claim 5, wherein said comparing means further comprises:
    means for reading the current outline data as a plurality of suboutline data corresponding to the different movement positions;
    additional storage means for storing the suboutline data; and
    additional comparison means for comparing the suboutline data with the updated reference outline data;
    wherein said disparity detecting means further comprises:
    means for determining a disparity in the cyclic length in accordance with the suboutline data which coincide with the updated reference outline data.

7. An apparatus according to claim 6, wherein the additional storage means has a plurality of memories for storing the suboutline data.

8. An apparatus according to claim 5, wherein said comparing means further comprises:

means for shifting a plurality of components of the current outline data and the updated reference outline data in accordance with the movement position data so as to obtain sequentially outline data components, and means for comparing sequentially the outline data components of the updated reference outline data with the outline data components of the current outline data, and wherein said disparity detecting means further comprises:

means for determining a disparate amount based on a number of coincidences between the outline data components of the current outline data and the updated reference outline data.

* * * * *